United States Patent [19]
Mirkovic

[11] Patent Number: 5,254,118
[45] Date of Patent: Oct. 19, 1993

[54] THREE DIMENSIONAL SPINE FIXATION SYSTEM

[76] Inventor: Srdjian Mirkovic, 600 N. McClurg Ct., Apt. 3805A, Chicago, Ill. 60611

[21] Appl. No.: 802,311

[22] Filed: Dec. 4, 1991

[51] Int. Cl.[5] .................................................. A61F 5/04
[52] U.S. Cl. .................................. 606/61; 606/60; 606/73
[58] Field of Search .................... 606/54, 60-64, 606/104, 87, 72, 73

[56] References Cited

U.S. PATENT DOCUMENTS

| | | | |
|---|---|---|---|
| 4,274,401 | 6/1981 | Miskew | 606/61 |
| 4,369,769 | 1/1983 | Edwards | 128/69 |
| 4,422,451 | 12/1983 | Kalamchi | 128/69 |
| 4,448,191 | 5/1984 | Rodnyansky et al. | 128/69 |
| 4,569,338 | 2/1986 | Edwards | 128/69 |
| 4,573,454 | 3/1986 | Hoffman | 128/69 |
| 4,604,995 | 8/1986 | Stephens et al. | 128/69 |
| 4,653,481 | 3/1987 | Howland et al. | 128/69 |
| 4,686,970 | 8/1987 | Dove et al. | 128/69 X |
| 4,696,290 | 9/1987 | Steffee | 606/61 |
| 4,763,644 | 8/1988 | Webb | 128/69 |
| 4,771,767 | 9/1988 | Steffee | 606/61 X |
| 4,773,402 | 9/1988 | Asher et al. | 128/69 |
| 4,790,297 | 12/1988 | Luque | 128/69 |
| 4,805,602 | 2/1989 | Puno et al. | 128/69 |
| 4,827,918 | 5/1989 | Olerud | 606/61 |
| 4,887,596 | 12/1989 | Sherman | 606/61 |
| 4,913,134 | 4/1990 | Luque | 128/69 |
| 4,944,743 | 7/1990 | Gotzen et al. | 606/61 |
| 4,950,269 | 8/1990 | Gaines, Jr. | 606/61 |
| 4,987,892 | 1/1991 | Krag et al. | 606/61 |
| 5,002,542 | 3/1991 | Frigg | 606/61 |
| 5,005,562 | 4/1991 | Cotrel | 128/69 |
| 5,007,909 | 4/1991 | Rogozinski | 606/61 |
| 5,047,029 | 9/1991 | Aebi et al. | 606/61 |
| 5,053,034 | 10/1991 | Olerud | 606/61 |
| 5,057,109 | 10/1991 | Olerud | 606/61 |
| 5,067,955 | 11/1991 | Cortel | 606/61 |
| 5,084,048 | 1/1992 | Jacob et al. | 606/61 |
| 5,084,049 | 1/1992 | Asher et al. | 606/60 X |

*Primary Examiner*—Robert A. Hafer
*Assistant Examiner*—Brian E. Hanlon
*Attorney, Agent, or Firm*—Laff, Whitesel, Conte & Saret

[57] ABSTRACT

A three dimensional spine fixation system includes a rigid rod spanning the length of spine to be fixed, a plurality of threaded fasteners to be embedded in the spine, and at least two connectors for connecting the rod to the fasteners. The connectors are extremely adaptable to virtually any desired path for the rod, being fixably movable longitudinally, transversely, or angularly relative to the fasteners, as well as rotationally about the fasteners and rotationally about a predetermined axis angled with respect to the fasteners. By properly positioning the connectors and fasteners, the rod can be easily positioned without bending for virtually any anatomy, due to the ability to move the connectors multi-axially and in three dimensions.

2 Claims, 3 Drawing Sheets

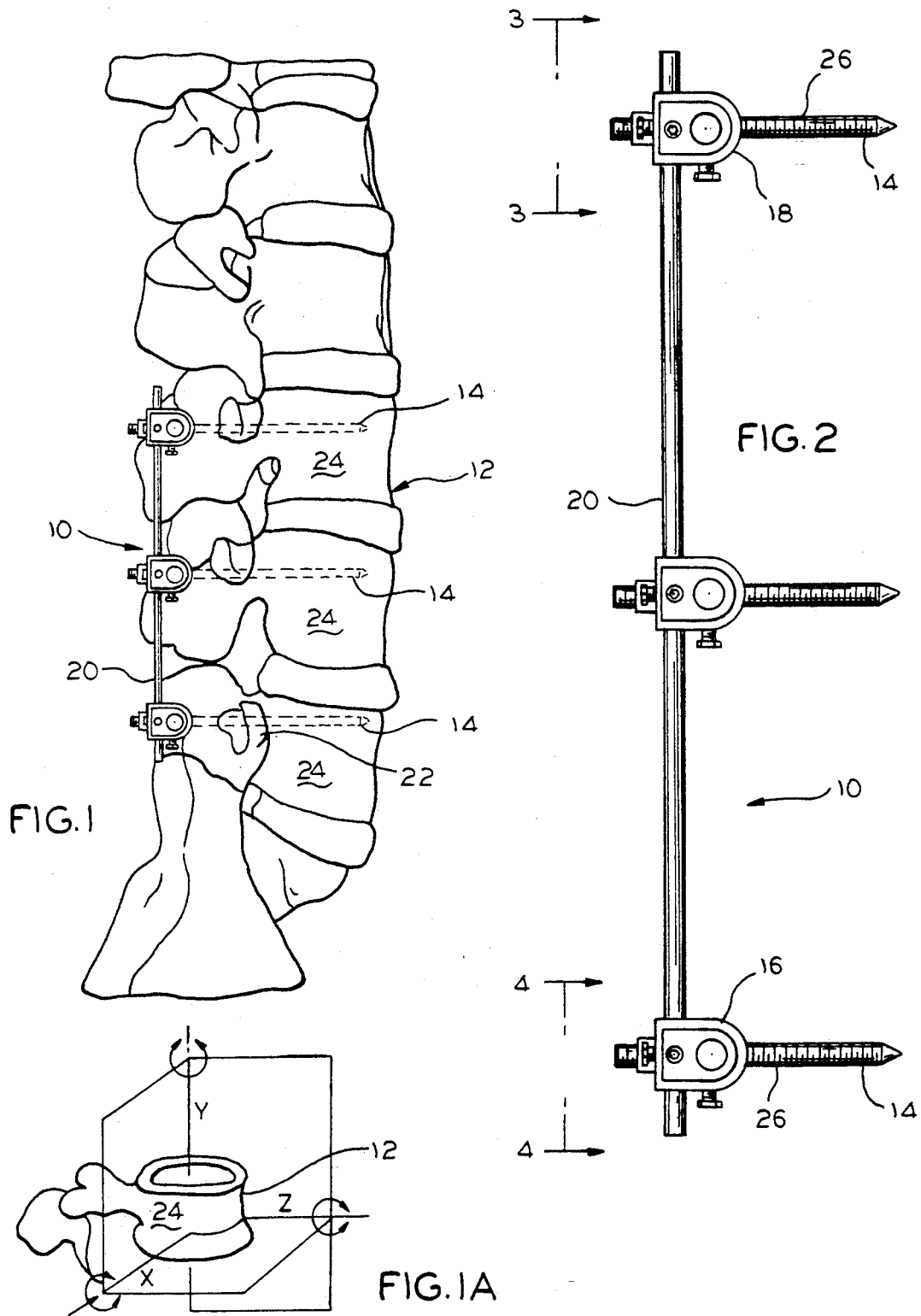

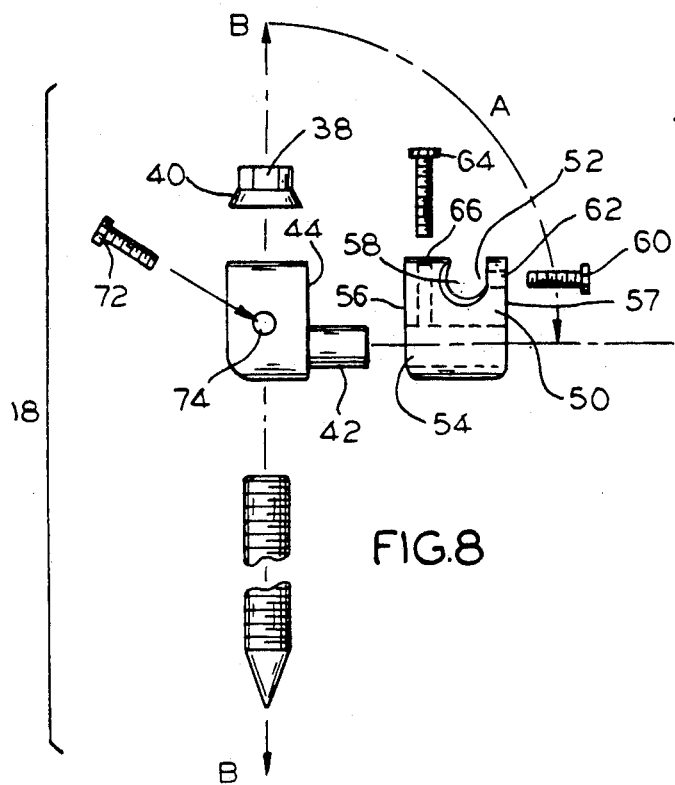
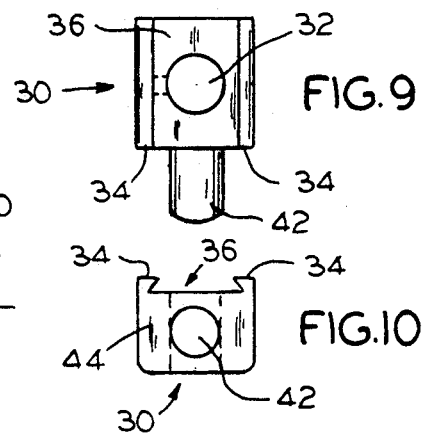
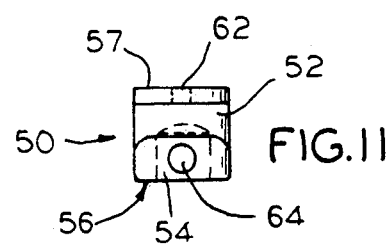
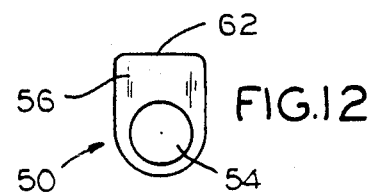
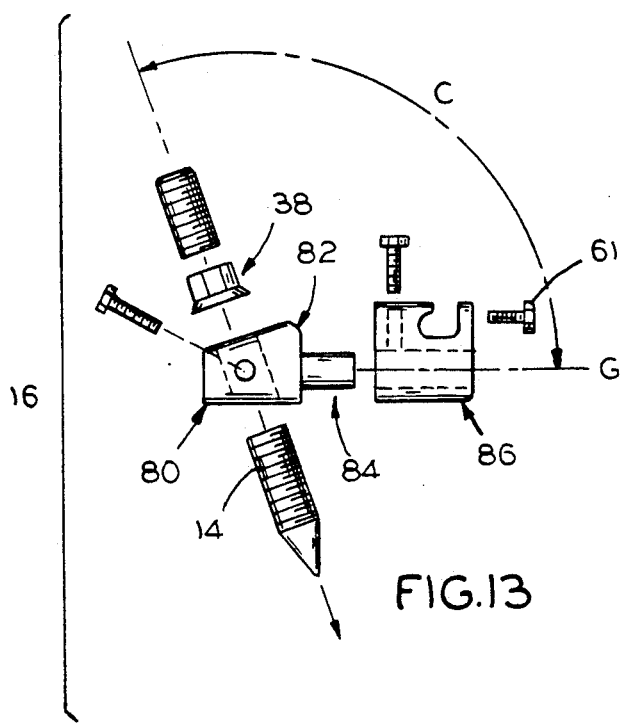
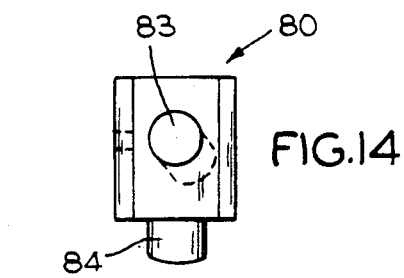
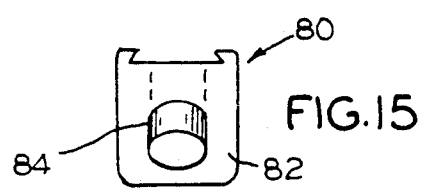

THREE DIMENSIONAL SPINE FIXATION SYSTEM

This invention relates to spinal instrumentation and, more particularly, to an internal spine fixation system.

BACKGROUND OF THE INVENTION

The human spine typically has a characteristic S-shape that, when deformed or injured, presents special problems to solve. The individual vertebrae comprising the spinal column can be displaced from their normal position in any one or more of the three dimensions, referred to herein as the X, Y, and Z axes. The X axis is defined as extending laterally, or side-to-side, across the human body. The Y axis is defined as extending longitudinally, or from head to foot, through the human body. The Z axis is defined as extending transversely, or from front to back, through the human body. Various events can cause deformation: fracture, slippage, tumors, and infections are examples. To correct the alignment of the vertebrae, it may be necessary to compress, distend, or rotate all or part of the spinal column along any one or more of X, Y, or Z axes.

To maintain the vertebrae in the desired alignment, a surgical fusion technique is often indicated. Fusion, however, is not usually successful unless the vertebrae are also fixed for a time period by a mechanical device installed internally during surgery. This allows the fused bone time to heal. Numerous mechanical devices or systems have been made for this purpose. Screw and rod systems and screw and plate systems are commonly used mechanical systems. The former system typically uses a rigid rod secured to the spine by screws inserted in the pedicles for holding the rod. The rod is bent to the desired configuration, and this both manipulates and holds the vertebrae in that same configuration until the fusion process can permanently accomplish the same thing. The latter system uses a rigid plate instead of a rod, and the plate is simply bolted with pedicle screws and nuts to the spinal column to again provide the desired configuration and rigidity to the spine.

Some screw and rod systems, however, suffer several disadvantages. In the lumbar sacral area, the proper curvature or alignment is sometimes lost after surgery because the rod disengages from the screw/rod connectors. Further, each patient has his or her own spinal characteristics or anatomy, including bone shape and density. Thus, the exact location of the system and the pedicle screws, and the exact configuration of the rigid rod, is determined while the patient is on the operating table. Bending the rod consumes operating time, because contouring the rod to correspond to the three-dimensional configuration of the spine can be extremely difficult and ca lead to mistakes.

The three dimensional anatomic orientation of the pedicle is also difficult to ascertain prior to surgery. Thus, screws inserted into the pedicle may frequently need to be re-orientated, and their depth of insertion readjusted. This often requires complete screw removal, particularly if spinal deformation was not exactly as anticipated or if the space available for the screw was insufficient. Removing and replacing screws jeopardizes the fragile bone structure of the pedicle around the screw holes, as well as consuming additional surgical time.

Plate systems suffer some of the same and other disadvantages. Since the plate is normally secured closer to the vertebral bodies than the rod, and the surfaces of the posterior structures of the vertebrae are uneven, more bone must be removed in order to properly position the plate. The plates also have more limited configurations because they are more difficult to bend over a long distance. As with a screw/rod system, the need for adjustment of the height of the screws, and often the removal and reinsertion of screws during the surgical implantation procedure to account for individual peculiarities in bone structure, frequently jeopardizes the integrity of the screw holes and the entire fixation process.

Due to the three dimensional configuration of the spine, the ideal system would be one which can be easily adjusted to this three dimensional configuration. The system would allow correction along the longitudinal (vertical) Y-axis, including compression, distraction, and rotational correction of the vertebrae around the Y-axis, such as seen in scoliosis. This system should also allow correction of the laterolisthesis along the transverse X-axis, as well as rotation around the X-axis which permits correction of kyphosis and lordosis. Finally, correction should be possible for displacement along the Z-axis forward/ anteriorly, known as anterolisthesis, or backwards/ posteriorly, known as retrolisthesis, as well as rotation around the Z-axis. At the present time, a system is not available which can allow the multi-directional, multi-axial correction over multiple bone segments (three or greater). Because of this, present systems-whether they are screw/rod, hook/rod or plate-all have limited usefulness allowing some, but not all needed corrections.

Thus, there is a need for a multi-directional, multi-axial fixation system which can restore the anatomic configuration no matter what the deformity. It should also permit easy manipulation and handling of instrumentation during surgery.

SUMMARY OF THE INVENTION

Accordingly, the present invention provides an internal spine fixation system comprising a rigid rod, single length screw fasteners for placement in the vertebral body, and multiple connectors mounted on the fasteners for retaining the rod between the fasteners. The proximal end of the fastener is embedded in the desired location in the vertebrae. The connectors include a first member having an aperture for receiving the top or distal end of a fastener, and a second member which is rotatable relative to the first member for receiving the rod. A longitudinal adjustment nut on each fastener engages the top of each first member for adjusting its position along each fastener. Each second member is slidably and rotatably attached to the first member along a slide pin extending between them, thereby allowing the spacing between the first and second members to be adjusted. Rotation of the second member around the slide pin permits capture of the rod at various angles. The entire connector can also be rotated around the fastener.

BRIEF DESCRIPTION OF THE DRAWINGS

A preferred embodiment of the invention is shown in the attached drawings wherein:

FIG. 1 is a side elevation view of the invention fixed to the spinal column;

FIG. 1A is a perspective view of a vertebral body and the X, Y and Z axes;

FIG. 2 is a side elevation view of the invention;

FIG. 8 is an exploded side elevation view of a connector and fastener;

FIG. 9 is a top plan view of the first member of the connector of FIG. 8;

FIG. 10 is a side elevation view of the first member of FIG. 8;

FIG. 11 is a top plan view of the second member of the connector of FIG. 8;

FIG. 12 is a side elevation view of the second member of the connector of FIG. 8;

FIG. 13 is an exploded side elevation view of another connector and fastener;

FIG. 14 is a top plan view of a first member of the connector of FIG. 13; and

FIG. 15 is a side elevation view of the first member of the connector of FIG. 13.

DESCRIPTION OF THE PREFERRED EMBODIMENT

Figure 3:
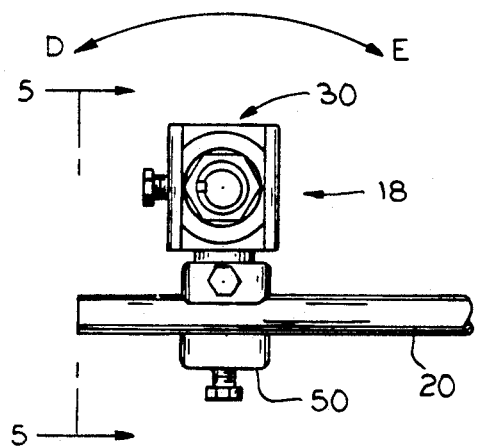
FIG. 3 is a top plan view of a connector and rod section of the invention as seen from line 3—3 of FIG. 2.

The inventive three-dimensional spine fixation system 10 shown in FIG. 2 can be positioned at the desired location along the spine in the thoracic, lumbar or sacral region. FIG. 1 shows an example of where the system 10 may be located in lumbar region 12. In general, the system 10 includes at least two threaded screws or fasteners 14, at least two connectors 16, 18 mounted on the screw, and a rigid, elongated rod 20 extending between the connectors. The fasteners 14 are preferably embedded in the pedicle bones 22 of the vertebral bodies 24 in the spine 12, with threads 26 formed along the fastener length. As described herein, the system can be used to manipulate the spine in any of the three dimensions defined by the X, Y, and Z axes (FIG. 1A).

FIGS. 3, 5, and 8-12 show in various detail connector 18. Connector 18 includes a first member 30 and a second member 50. First member 30 has a smooth bore aperture 32 extending from top to bottom in sufficient diameter to permit passage of fastener 14. The top of first member 30 includes a pair of opposing guides 34 and a channel 36 between them. A height adjusting nut 38, internally threaded to receive and engage a fastener 14, fits on top of first member 30 in coaxial alignment with aperture 32. The nut has a skirt flange 40 which is received in channel 36 and slidably engaged beneath guides 34. First member 30 also includes a slide pin 42 extending away from side 44 of first member 30. Slide pin 42 projects at an angle A relative to the longitudinal axis B of fastener 14. In connector 18, side 44 of first member 30 lies in a plane parallel to the longitudinal axis B of fastener 14, and angle A is 90 degrees relative to both side 44 and axis B.

Figure 5:
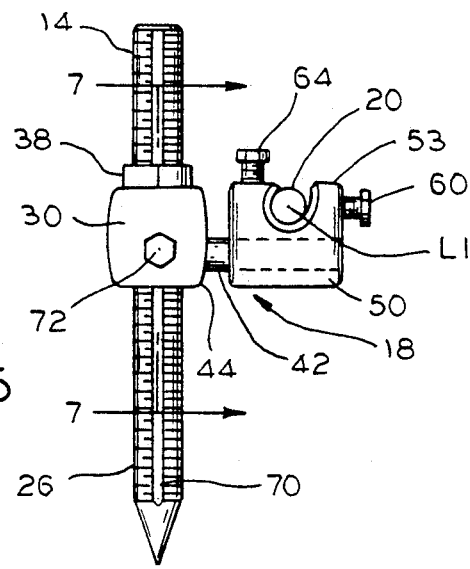
FIG. 5 is a side elevation view of the connector of FIG. 3 as seen from line 5—5 and mounted on a fastener.

Second member 50 of connector 18 is shown in FIGS. 3, 5, 8, 11 and 12. Second member 50 has an open rod-receiving slot 52 extending downwardly from an upper surface 53 of second member 50 and across its width for receiving rod 20. Second member 50 also has a slide pin-receiving cavity 54 in first end face 56 extending longitudinally partially through the member and offset radially from the center of first end face 56. Second end face 57 is opposite and parallel to first end face 56 and, when mounted on slide pin 42, also to side 44 of first member 30. When mounted on slide pin 42, second member 50 is rotatably moveable around slide pin 42. Slot 52 is larger than the diameter of rod 20 so as to easily receive it, and slot 52 desirably has a press-fit notch 58 to more securely retain the rod. A set screw 60 extending through hole 62 is used to lock the rod 20 within the slot. Cavity 54 is larger than slide pin 42 so as to easily receive it. Set screw 64 (FIG. 5) extending through hole 66 is used to lock second member 50 in a desired location spaced apart from fastener 14 so as to position rod 20 at location $L_1$ relative to the X axis (FIG. 5).

Figure 7:
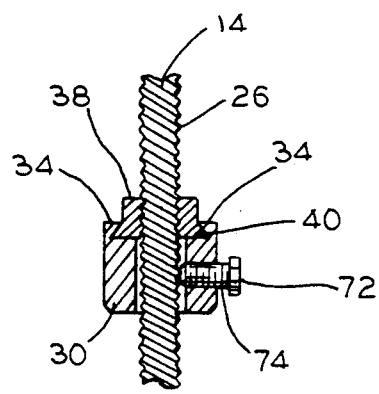
FIG. 7 is a cross-sectional view of the connector and fastener of FIG. 5 taken along line 7—7.

A fastener 14 may be inserted and locked into connector 18 as best shown in FIGS. 5 and 7. The height adjusting nut 38 has been positioned into channel 36 of first member 30 so that skirt flange 40 is engaged beneath guides 34. The fastener 14 has threads 26 extending around its circumference, except that a groove 70 runs substantially the length of fastener 14 and interrupts the threads. The fastener engages the mating threads of height adjusting nut 38 and passes through aperture 32 of first member 30. A set screw 72 is inserted through hole 74 in first member 30 to bear against groove 70 and thereby resist inadvertent rotation of connector 18, which would change its position along fastener 14.

For many applications of the invention, the longitudinal axis B of fastener 14 is generally parallel to the Z axis and perpendicular to the XY plane. For certain applications, however, such as placement of fastener 14 in the L5 and S1 pedicles of the spine, fastener 14 would have to be placed at an angle other than 90 degrees to the XY plane, in which case it is useful to adapt the connector.

Connector 16 has been designed for this purpose. Connector 16, best shown in FIGS. 6 and 13-15, is constructed in much the same way as connector 18, with a few important differences. Connector 16 is attached to a fastener 14 through aperture 83 and to a height adjusting nut 38 in the same manner as connector 18. The aperture 83 of connector 16, in contrast to aperture 32 of connector 18 is drilled at an angle other than 90 degrees relative to the XY plane. The fastener 14 is consequently correspondingly angled within first member 80 relative to the XY plane. This angle compensates for the orientation of the L5 and S1 pedicles so that slide pin 84 and second member 86 are at the desired positions closely parallel to the XY plane, thereby minimizing bending of the interconnecting rod. The slide pin 84 extends perpendicularly away from side 82 of first member 80 and at angle C relative to the longitudinal axis B of fastener 14. Angle C may be greater or less than 90 degrees, depending on the specific location on L5 or S1 where the fastener is to be placed. Second member 86 is connected to first member 80 and spaced apart from fastener 14 along slide pin 84 so as to hold the rod 20 at location $L_2$ relative to the X axis. When mounted on slide pin 84, second member 86 is also rotatably movable around slide pin 84.

Two or more connectors are used with a rod 20 to position and fix the spine. A surgeon may choose connectors all of the configurations exemplified by connector 18, or of the configuration exemplified by connector 16, or a combination of both configurations. Different spinal problems dictate that the rod be positioned in different ways, and the spinal locations available for anchoring the rod sometimes require a connector capable of multi-axial and multi-dimensional movement.

Figure 6:
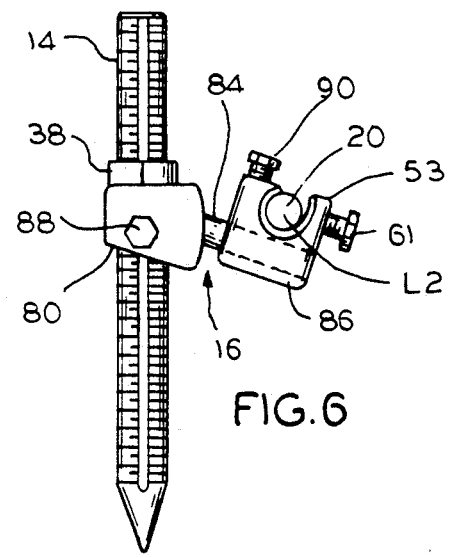
FIG. 6 is a side elevation view of the connector of FIG. 4 as seen from line 6—6 and mounted on a fastener.

The invention provides the capability of manipulating the spine in three dimensions. Referring to FIGS. 5 and 6, spinal movement or corrections along the X axis are possible by sliding second members 50 and 86 toward and away from the fastener 14 along slide pins 42 and 84, respectively. Rotation around the X axis is possible by loosening set screws 64 and 90 and rotating second members 82 and 50, respectively, around slide pin axes F and G, respectively, as shown in FIGS. 8 and 13. This movement is useful to correct kyphosis or lordosis.

Spinal movement or corrections along the Y axis are possible by embedding at least two fasteners in the appropriate vertebral bodies, loosely placing the rod within the connectors, compressing or distracting the fasteners using standard orthopedic technique, and then locking the rod into the connectors by tightening set screws 60 and 61 while the spine is held in its compressed or distracted state so that the rod then maintains the spine as desired along the Y axis. Rotation around the Y axis, such as seen in the rotation of the vertebrae in scoliosis, is achieved by advancing the adjustment nut 38 down a fastener 14 embedded in the vertebral body (i.e., toward the vertebral body) with the rod locked to the connector, thereby pushing the vertebral body on one side forward or anteriorly. Simultaneously, by advancing the adjustment nut 38 up the fastener (away from the vertebral body) on the opposite side of the vertebral body, the vertebral body is pulled posteriorly. This push/pull action on opposite sides of the vertebral bodies allows vertebral body rotation around the Y axis.

Figure 4:
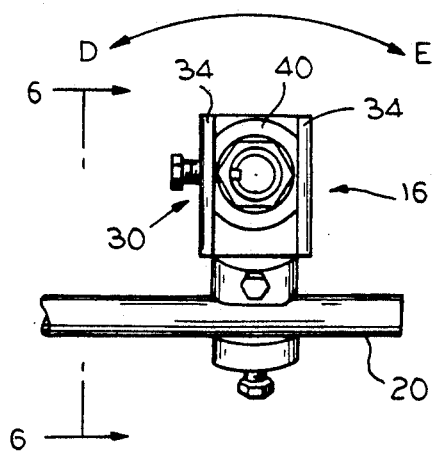
FIG. 4 is a top plan view of a different connector and rod section of the invention as seen from line 4—4 of FIG. 2.

Spinal movement or corrections along the Z axis are possible by rotating height adjustment nut 38 and thereby also moving connector 18 or 16 along fastener 14 before the rod is locked to the connectors. This movement is useful to correct antero- and retrolisthesis. It is thus unnecessary to rotate the entire connector to change the position of connector 18 or 16 along fastener 14. Rotation around the Z axis can be accomplished by loosening set screws 72 and 88 (FIGS. 3 and 4) so that connectors 18 and 16 can be rotated relative to the fastener 14 in direction D or E. This is useful in facilitating correction of compression or distraction.

Once the connectors are positioned as desired, the rod 20 can be locked into the slots 52 using set screws 60 or 61. Once the rod is finally positioned within the connectors, the top portions of fasteners 14 above the height adjustment nuts 38 can be cut off.

There are numerous advantages to the inventive system. The multi-dimensional adjustability of the connectors adapts to virtually any anatomy and spinal problem easily, and substantially diminishes the need to bend the rod to conform to the desired spinal shape. The height adjustment means permits easy Z axis adjustments, and it also permits the use of a single length screw rather than screws of different lengths to accommodate various spinal deformities or locations, thus avoiding the need to change screws. This is a particularly useful advantage considering the unavoidable bony loss associated with screw changing. The rotational capabilities of the connectors about multiple axes (the fastener axis B and the slide pin axis F o G) further contributes to the system's effectiveness, adaptability, and ease of use.

Those who are skilled in the art will readily perceive how to modify the invention and its three-dimensional capabilities. Therefore, the appended claims are to be construed to cover all equivalent structures which fall within the true scope and spirit of the invention.

The invention claimed is:

1. An internal spine fixation system comprising:
    a rigid elongated means for positioning over said spine;
    a plurality of fasteners, each having a longitudinal dimension with a proximal end for securing to said spine at a preselected location, and a distal end, said fasteners also each having a linear groove extending longitudinally along substantially the entire length of said fasteners;
    means for connecting said elongated means to said fasteners, said connecting means each having a first member mounted on said distal end of said fasteners, said connecting means further having a second member connected to said first member along a slide pin extending between said first and second members at an angle relative to said longitudinal dimension of said fastener, said connecting means movable longitudinally and rotationally along substantially the entire length of said fasteners to a desired fixed position, said second member also movable to a desired fixed position toward or away from said fasteners along said slide pin;
    said connecting means further having an upper surface with an open slot for receiving said elongated means, said slot extending downwardly from said upper surface and across the width of said connecting means;
    means for locking said elongated means within said slot; and
    means engaging both said connecting means and said fastener grooves so as to lock said connecting means to said fasteners at a selected location anywhere along substantially the entire length of said fastener and to resist rotation of said connecting means around said fasteners;
    whereby engagement of said connecting means with said groove provides rigid fixation of said fastener, elongated means and connecting means by limiting rotational and translational movement around and along said fastener.

2. An internal spine fixation system comprising:
    elongated means for providing rigidity to the spine;
    a plurality of connectors for attachment to said elongated means, said connectors each having a first member with an aperture extending through said first member, and a second member having a rod-receiving slot, said first member slidably connected to said second member along a slide pin extending between said first and second members, said second member mounted for rotation about said slide pin;
    means for locking said second member anywhere along substantially said entire slide pin so as to fix the rotational and translational position of said second member relative to said first member;
    a fastener for each of said first members having a proximal end and a distal end, said distal end for engagement with one of said apertures in said connectors and said proximal end for affixation in said spine;

a height adjustment means engaging each of said connectors for selectively changing the position of each of said connectors along the length of said fasteners and the height of said connectors above said proximal end; and wherein each of said first members has a pair of parallel guides along its top surface, said guides defining a channel between them, and wherein said height adjustment means comprises a nut for engagement with each of said fasteners, said nut having a flange seated in said channel and lockingly engaged beneath said guides, whereby rotation of said nut moves said first member along the length of said fastener.

* * * * *